United States Patent [19]

Deguchi et al.

[11] Patent Number: 5,154,850
[45] Date of Patent: Oct. 13, 1992

[54] NEUTRAL LIQUID DETERGENT COMPOSITION

[75] Inventors: Katsuhiko Deguchi; Kozo Saito; Hiroyuki Saijo, all of Utsunomiya, Japan

[73] Assignee: Kao Corporation, Tokyo, Japan

[21] Appl. No.: 790,061

[22] Filed: Nov. 12, 1991

Related U.S. Application Data

[63] Continuation of Ser. No. 544,903, Jun. 28, 1990, abandoned.

[30] Foreign Application Priority Data

Jul. 18, 1989 [JP] Japan .................. 1-184980

[51] Int. Cl.⁵ .............................................. C11D 1/66
[52] U.S. Cl. .................... 252/174.17; 252/DIG. 1; 252/DIG. 5; 252/DIG. 13; 252/DIG. 14
[58] Field of Search ...................... 252/174.17, 174.22, 252/DIG. 1, DIG. 5, DIG. 13, DIG. 14

[56] References Cited

U.S. PATENT DOCUMENTS

| | | | |
|---|---|---|---|
| 3,549,539 | 12/1970 | Mallows | 252/99 |
| 3,925,224 | 12/1975 | Winston | 252/89 |
| 4,088,598 | 5/1978 | Williams | 252/135 |
| 4,154,706 | 5/1979 | Kenkare et al. | 252/547 |
| 4,240,921 | 12/1980 | Kaniecki | 252/156 |
| 4,332,692 | 6/1982 | Payne et al. | 252/135 |
| 4,369,134 | 1/1983 | Deguchi et al. | 252/526 |
| 4,627,931 | 12/1986 | Malik | 252/153 |
| 4,663,069 | 5/1987 | Llenado | 252/117 |
| 4,668,422 | 5/1987 | Malik et al. | 252/174.17 |
| 4,708,813 | 11/1987 | Snyder | 252/90 |
| 4,897,214 | 1/1990 | Gazzani | 252/170 |
| 4,948,528 | 8/1990 | Hoeffkes et al. | 252/357 |
| 4,963,535 | 10/1990 | Sekag et al. | 514/54 |
| 4,968,450 | 11/1990 | Kamegai et al. | 252/545 |

FOREIGN PATENT DOCUMENTS

| | | |
|---|---|---|
| 0540798 | 5/1957 | Canada . |
| 0075995 | 4/1983 | European Pat. Off. . |
| 0105556 | 4/1984 | European Pat. Off. . |
| 0360743 | 3/1990 | European Pat. Off. . |
| 2358877 | 2/1978 | France . |
| 1540386 | 2/1979 | United Kingdom . |

OTHER PUBLICATIONS

"Calculation of HLB Values of Nonionic Surfactants", Griffin, *The American Perfumer*, May 1955.

*Primary Examiner*—Paul Lieberman
*Assistant Examiner*—Kery A. Fries
*Attorney, Agent, or Firm*—Oblon, Spivak, McClelland, Maier & Neustadt

[57] ABSTRACT

A neutral liquid detergent composition is disclosed. The composition comprises: (a) 2–60% by weight of an alkyl glycoside; (b) 0.1–10% by weight of a nonionic surfactant having an HLB of less than 5; (c) 0.1–10% by weight of a nonionic surfactant having an HLB of not less than 5; and (d) 0.001–8% by weight of one or more water-soluble organic or inorganic salts. The composition exhibits reduced irritation and damage to the hair or the skin, and high foaming ability. It imparts a favorable feeling upon use. After washing, the detergent components can easily be rinsed off leaving the least amount of water on the washed tableware.

2 Claims, No Drawings

NEUTRAL LIQUID DETERGENT COMPOSITION

This application is a continuation of application Ser. No. 07/544,903, filed on Jun. 28, 1990, now abandoned.

BACKGROUND OF THE INVENTION

1. Field of the Invention

The present invention relates to a detergent composition, and, more particularly, to a neutral liquid detergent composition exhibiting remarkably reduced irritation and damage to the hair or the skin, possessing high foaming ability, and imparting a favorable feeling upon use. The detergent composition has also good rinsability of foam and excellent drainability from tableware and the like after washing.

2. Description of the Background Art

Because of increased awareness for safety towards the human body in recent years, a number of trials have been undertaken in order to moderate the action of detergent compositions which frequently contact the skin. Such detergent compositions include laundry detergents, dishwashing detergents, household detergents, hair shampoos, and body shampoos. One of the approaches is adjusting the pH of detergent compositions to a weakly acidic range, e.g. pH 5-6, close to the intrinsic pH of human skins so as to be mild to the skin. Another approach is to incorporate low irritant components as major detergent base components. For example, amino acid surfactants, alkyl phosphate surfactants, or the like are being used as a low irritant detergent (Japanese Patent Publication Nos. 40125/1975, 426023/1976, 9033/1980, and 27319/1983).

Even though these surfactants are low irritant, they do not necessarily exhibit sufficient detergency and foaming ability is also their drawback. On the other hand, sodium alkylbenzenesulfonates have conventionally been popular detergent base components for dishwashing detergents because of their strong detergency. The compounds, however, give a strong defattying action to the skin and thus can be a cause of roughened hands.

Because of these reasons, sodium alkylethoxysulfates which are less irritant to the skin have gained a wider popularity as the base components for dishwashing detergents in recent years. Their detergent performances are even promoted by incorporating co-surfactants such as tertiary alkyl amine oxides, higher fatty acid diethanolamides, and the like. Their mildness to the skin is also improved by such a combination as compared with conventional detergent compositions.

The mildness to the skin of the detergents has improved to some degree as described above, nevertheless the achievement at present is still unsatisfactory.

Alkyl glycosides, being saccharide-derived surface active agents, are less irritant compounds. Although they are nonionic surfactants, it is well known that they not only produce stable foam themselves but also can act as a foam stabilizer for anionic surfactants. Thus, alkyl glycosides are gaining much attention in recent years. Japanese Patent Laid-open No. 104625/1983, for example, discloses a foaming surfactant composition comprising an alkyl glycoside and an anionic surface active agent, and Japanese Patent Laid-open No. 74999/1987 discloses a liquid dishwashing detergent composition comprising an alkyl glycoside, an anionic surface active agent, and a fatty acid alkanolamide. They claim that the compositions are low irritant and have an excellent detergency. Even though these detergent compositions exhibit performances better than conventional detergent compositions containing polyoxyethylenealkylethers as a base component, such performances are still to be improved. They have problems such as an inferior feeling upon use, poor rinsability of the foam, and insufficient drainability.

In view of this situation, the present inventors have conducted extensive studies to make the maximum use of the characteristics of alkyl glycosides, and found that a detergent composition which exhibits an excellent feeling upon use, good rinsability of the foam, and superior drainability by incorporating alkyl glycosides together with a specific amount of certain type of nonionic surfactant having a specific HLB other than alkyl glycosides and a specific amount of certain type of water-soluble salt. Such findings have led to the completion of this invention.

SUMMARY OF THE INVENTION

Accordingly, an object of the present invention is to provide a neutral liquid detergent composition comprising:

(a) 2-60% by weight of an alkyl glycoside represented by the following formula (I):

$$R_1(OR_2)_xGy \qquad (I)$$

wherein $R_1$ is a linear or branched alkyl, alkenyl, or alkylphenyl group having 8-18 carbon atoms, $R_2$ is an alkylene group having 2-4 carbon atoms, G is a reducing saccharide residue having 5-6 carbon atoms, x is a number of which the mean value is 0-5, and y is a number of which the mean value is 1.0-1.42;

(b) 0.1-10% by weight of a nonionic surfactant having an HLB of less than 5;

(c) 0.1-10% by weight of a nonionic surfactant having an HLB of not less than 5; and (d) 0.001-8% by weight of one or more water-soluble organic or inorganic salts selected from the group consisting of sulfates, chlorides, borates, phosphates, p-toluenesulfonates, m-xylenesulfonates, benzoates, malates, succinates, tartarates, citrates, lactates, and edates of sodium and potassium; the ratio by weight of components [(b)+(c)]/(a) being in a range of 1/10-1/1 and the ratio by weight of components (b)/(c) being in a range of 1/10-1/1.

Other objects, features and advantages of the invention will hereinafter become more readily apparent from the following description.

DETAILED DESCRIPTION OF THE INVENTION AND PREFERRED EMBODIMENTS

Alkyl glycoside, component (a) of the present invention, is used as a major surfactant in the composition of the present invention. The mean value of x in formula (I), being defined as 0-5, affects the water-solubility and crystalline property of the alkyl glycosides. Higher the value x, are the alkyl glycosides more soluble in water and less crystalline. A desirable value of x is in the range of 0-2.

When the value y in formula (I) is larger than 1, i.e., when alkyl glycosides contain those having di- or higher saccharides as the hydrophilic groups, the saccharide chain bonds may be 1-2, 1-3, 1-4, 1-6, α-pyranoside, β-pyranoside, or franoside, or a mixture thereof. Among the preferable value of y which is 1.0-1.42, a most preferable range is about 1.10–1.40. The value y is determined by the proton NMR method.

$R_1$ in formula (I) is a $C_{8-18}$ linear or branched alkyl, alkenyl, or alkylphenyl group. From the aspect of water-solubility and foaming ability, a preferable carbon number is $C_{10-14}$. $R_2$ in formula (I) is a $C_{2-4}$ alkylene group. From the aspect of water-solubility and the like, a preferable carbon number is $C_{2-3}$. The structure of G in formula (I) depends upon whether it represents a monosaccharide or a di- or higher saccharide. Monosaccharides include glucose, galactose, xylose, mannose, lyxose, arabinose, and the like, as well as their mixtures. Examples of di- or higher saccharides are maltose, xylobiose, isomaltose, cellobiose, gentiobiose, lactose, sucrose, nigerose, turanose, raffinose, gentianose, melezitose, and the like, as well as their mixtures. Among these, from the aspect of availability and cost, preferable monosaccharides are glucose and fructose, and preferable di-or higher saccharides are maltose and sucrose.

Component (a) is incorporated in the composition of the present invention in an amount of 2–60%, preferably 10–40% by weight.

Component (b) of the present invention is nonionic surfactants having an HLB value of less than 5. The HLB value is defined as the value calculated from the equation, J. T. Davies and E. K. Rideal: *Interfacial Phenomena*, pp 371–383 (1963), Academic Press, N.Y.

$$HLB = 7 + \Sigma \text{ (number of hydrophilic groups)} - \Sigma \text{ (number of hydrophobic groups)}$$

The number of each atomic group used for the HLB calculation is as follows.

| Atomic group | number of groups |
|---|---|
| Hydrophilic group | |
| Ester (sorbitan ring) | 6.8 |
| Ester (free) | 2.4 |
| —COOH | 2.1 |
| OH (free) | 1.3 |
| —O— | 0.5 |
| OH (sorbitan ring) | 0.5 |
| Lipophilic group | |
| $\underset{\mid}{-\text{CH}-}$ | 0.475 |
| —CH$_2$— | 0.475 |
| CH$_3$— | 0.475 |
| =CH— | 0.475 |
| Induction group | |
| —(CH$_2$—CH$_2$—O)— | 0.33 |
| —(CH$_2$—CH—O)—$\underset{\text{CH}_3}{\mid}$ | 0.15 |

Examples of component (b) are polyoxyethylene alkyl ether, polyoxyethylene alkylphenyl ether, polyoxyethylene sorbitan fatty acid ester, polyoxyethylene sorbit fatty acid ester, polyoxyethylene glycol fatty acid ester, polyoxyethylene polyoxypropylene alkyl ether, polyoxyethylene castor oil, polyoxyethylene hydrogenated castor oil, polyoxyethylene alkylamine, glycerol fatty acid ester, and the like. Component (b) is incorporated in the composition of the present invention in an amount of 0.1–10%, preferably 0.5–8% by weight.

Component (c) of the present invention is nonionic surfactants having an HLB value of not less than 5. Enumerated as examples of component (c) are polyoxyethylene alkyl ether, polyoxyethylene alkylphenyl ether, polyoxyethylene sorbitan fatty acid ester, polyoxyethylene sorbit fatty acid ester, polyethylene glycol fatty acid ester, polyoxyethylene polyoxypropylene alkyl ether, polyoxyethylene castor oil, polyoxyethylene hydrogenated castor oil, polyoxyethylene alkylamine, polyoxyethylene fatty acid amide, and the like having the total adduct mols of ethylene oxide of not less than 10.

Component (c) is incorporated in the composition of the present invention in an amount of 0.1–10%, preferably 0.3–8% by weight.

The ratio of component [(b)+(c)]/(a) is in the range of 1/10–1/1, preferably 1/8–1/1.5 by weight. The ratio of component (b)/(c) is in the range of 1/10–1/1, preferably 1/8–1/1.5 by weight.

The difference in HLB between component (b) and component (c) is preferably greater than 3.

Component (d) used in the present invention is water-soluble organic or inorganic salt given in the aforementioned explanation. Among them, sulfates, chlorides, borates, p-toluensulfonates, benzoates, citrates, and edates of sodium and potassium are particularly preferable.

The composition of the present invention contains 0.001–8% by weight of component (d). A preferable amount of component (d) is 0.01–5%, and particularly 0.1–4% by weight. The amount exceeding 8% by weight not only impairs the intended effects, but also adversely affects the stability of the composition.

Besides the above essential components, the composition of the present invention may comprise one or more of surfactants selected from the groups consisting of anionic surfactants (1–20% by weight), amphoteric surfactants (1–20% by weight), and nonionic surfactants (1–10% by weight) other than the above components (a)–(c). These surfactants are optionally incorporated into the composition of the present invention in order to promote its detergency and foaming ability. conventionally known anionic or amphoteric surfactants can be used. Such surfactants may include, for example, α-olefin sulfonates [$C_{8-20}$; Na, K, Mg, triethanolamine (TEA), NH$_4$ salts], polyoxyethylene alkylsulfates (EO=2–8; alkyl group: $C_{8-18}$, linear or branched; Na, K, Mg, TEA, NH$_4$ salts), salts of α-sulfo-fatty acid ester represented by the formula,

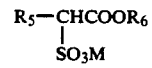

(wherein $R_5$: $C_{8-18}$, $R_6$: $C_{1-4}$, M: alkali metal), M-acylglutamates (acyl group: $C_{8-18}$; Na, K, TEA salts), monoalkyl phosphates (alkyl group: $C_{8-18}$; Na, K, TEA, arginine salts), linear alkylbenzenesulfonates (alkyl group: $C_{10-18}$; Na, K, Mg salts), alkyl betaine, alkyl sulfobetaine, alkyl hydroxysulfobetaine, and the like. Given as examples of the nonionic surfactants other than component (a)–(c) are mono- or di-alkanol ($C_{2-3}$) amides of $C_{3-22}$ fatty acid, tert-alkylamine oxides (alkyl group: $C_{8-18}$, linear or branched), and the like.

The pH range of a neat liquid of the detergent composition of the present invention is preferably 6–8, particularly 6.5–7.5 is most preferable.

In addition to the above components, other optional ingredients can be formulated into the composition of the present invention to the extent that its stability, detergency, and foaming ability are not adversely affected. Such optional components include lower aliphatic alcohols, e.g. ethanol; solubilizers, e.g. urea; viscosity adjusting agents, e.g. clay minerals, water-soluble polymers; water-insoluble abrasives, e.g. calcite, silica, calcium phosphate, zeolite, polyethylene, nylon, polystyrene; moisturizing agents, e.g. glycerol, sorbitol; feeling improvers, e.g. cationized cellulose; enzymes; perfumes; pigments; antiseptics; antifungal agents; and the like.

The detergent composition of the present invention thus prepared has excellent foaming ability, is mild to the skin and the hair, and imparts a favorable feeling to the hands during and after use. The foam is easily rinsed off and after washing water is easily drained from the tableware and the like. Thus, it is a neutral detergent composition having a high practical value.

Other features of the invention will become apparent in the course of the following description of the exemplary embodiments which are given for illustration of the invention and are not intended to be limiting thereof.

EXAMPLES

Example 1

The detergent compositions having the formulations shown in Table 1 were prepared. Their foaming ability, rinsability, feeling to the hands during and after use, and drainability were evaluated. The results are shown in Table 1.

The feeling to the hands during and after use was tested using composition A (Composition 11 in Table 1) as a standard. Evaluation was made by comparing the feelings given to the hands when composition A and composition B (Compositions 1-10 in Table 1) were used.

Test Methods and Evaluation Standards (1) Foaming ability

Foaming ability was measured on samples prepared by adding a commercially available butter in an amount of 0.1%, as a dirt component, to 0.5% detergent composition solutions. Forty milliliters of the solution of the detergent composition to which butter was added was charged into a glass cylinder with a diameter of 5 cm and subjected to a rotational stirring for 10 minutes. The height of the foam produced was measured after the termination of the stirring.

(2) Rinsability

Three liters of a sample solution with 0.25% detergent concentration was charged into a container (diameter: 30 cm, height: 12 cm) and rotationally stirred for 10 minutes, after which the liquid was discharged through an opening at the bottom of the container, leaving the foam in the container. Three liters of tap water was then charged to the container, and the ten-minutes stirring and discharge of liquid were repeated. This procedure was repeated until no foam was observed in the container. The number of times of tap water charge and discharge required for the foam to diminish was taken as the standard of rinsability.

(3) Feeling to the hands during and after use

Two 10% detergent composition solutions, A and B, at 40° C. were charged into 2-liter beakers. Feeling of solutions A and B to the hands was sensuously evaluated according to the following standard.

(i) Feeling of the solution

Hands were dipped into solutions A and B, i.e., one hand to solution A and the other to solution B. After 1 minute, the feeling to the hands was compared according to the following standard.

| | |
|---|---|
| B is less slimy than A | +2 |
| B is slightly less slimy than A | +1 |
| Hard to tell which is more slimy | 0 |
| B is slightly more slimy than A | −1 |
| B is more slimy than A | −2 |

(ii) Feeling after use

After the above test, the hands were thoroughly washed with water and wiped out with a dry towel. Then feeling of the hands were compared according to the following standard.

| | |
|---|---|
| B is less sticky than A | +2 |
| B is slightly less sticky than A | +1 |
| Hard to tell which is more sticky | 0 |
| B is slightly more sticky than A | −1 |
| B is more sticky than A | −2 |

The above tests were carried out by 10 panelists. The total scores gained by solution B was taken as the feeling of the solution B.

(4) Drainability

Three liters of a 0.15 % detergent composition solution (in 3.5° DH at 25° C.) was charged into a container (diameter: 30 cm, depth: 12 cm). A piece of porcelain dish having a 25 cm diameter was dipped into the solution for 3 minutes. The dish was taken out from the solution and dried at 25° C. This procedure was repeated 4 times. Then the dish was again dipped into the solution, following which it was taken out from the solution and rinsed for 30 seconds in a water stream and dried. The number of water spots remaining on the surface of the dish was counted to evaluate the drainability according to the following standard. Evaluation Standard:

A: No water spots are present
B: Less than 20 water spots are present
C: 20 or more of water spots are present

TABLE 1

| Component | % by weight Example Compositions | | | | | |
|---|---|---|---|---|---|---|
| | 1 | 2 | 3 | 4 | 5 | 6 |
| Component (a) | | | | | | |
| Alkyl glycoside: in formula (I), $x = 0$, G = glucose residue, | | | | | | |
| $R_1$: $C_{9-11}$ alkyl, y = 1.2 | 23 | 23 | — | — | 23 | — |
| $R_1$: $C_{9-11}$ alkyl, y = 1.42 | — | — | 23 | 23 | — | 23 |
| Component (b) | | | | | | |
| Polyoxyethylene (p = 3) | 3 | — | — | 4 | — | 10 |

TABLE 1-continued

| | | | | | | |
|---|---|---|---|---|---|---|
| lauryl ether (HLB = 2.8) | | | | | | |
| Glycerol monooleate (HLB = 2.5) | | 3 | — | — | 1 | — |
| Sorbitan monostearate (HLB = 4.9) | — | — | 1 | — | — | — |
| Component (c) | | | | | | |
| Polyoxyethylene (p̄ = 15) lauryl ether (HLB = 6.8) | 5 | — | — | 4 | — | — |
| Polyethylene glycol (MW = 3000) monostearate (HLB = 23.7) | — | 5 | — | — | 10 | — |
| Polyoxyethylene (p̄ = 20) polyoxypropylene (p̄ = 5) myristyl ether (HLB = 8.2) | — | — | 2 | — | — | — |
| Polyoxyethylene (p̄ = 20) sorbitan monolaurate (HLB = 14.3) | — | — | — | — | — | 10 |
| Component (d) | | | | | | |
| NaCl | 0.5 | — | — | — | — | — |
| $K_2SO_4$ | — | 0.5 | — | 0.2 | — | — |
| Sodium citrate | — | — | 0.5 | — | — | 3 |
| Sodium p-toluenesulfonate | — | — | — | 0.3 | — | — |
| Disodium edate | — | — | — | — | 0.5 | — |
| Water | Balance | Balance | Balance | Balance | Balance | Balance |
| pH 1) (neat liquid) | 6.8 | 7.0 | 7.1 | 6.3 | 7.8 | 7.0 |
| Evaluation | | | | | | |
| Foaming ability (mm) | 92 | 90 | 87 | 90 | 88 | 85 |
| Rinsability (times) | 5 | 5 | 5 | 5 | 5 | 5 |
| Felling to the hands | | | | | | |
| During use | +9 | +8 | +8 | +9 | +8 | +8 |
| After use | +9 | +8 | +8 | +9 | +8 | +8 |
| Drainability | A | A | A | A | A | A |

| | % by weight Comparative Compositions | | | | |
|---|---|---|---|---|---|
| Component | 7 | 8 | 9 | 10 | 11 |
| Component (a) | | | | | |
| Alkyl glycoside: in formula (I), x = 0, G = glycose residue. | | | | | |
| $R_1$: $C_{9-11}$ alkyl, y = 1.2 | 23 | 23 | — | — | 23 |
| $R_1$: $C_{9-11}$ alkyl, y = 1.42 | — | — | 23 | 23 | — |
| Component (b) | | | | | |
| Polyoxyethylene (p̄ = 3) lauryl ether (HLB = 2.8) | 3 | — | — | — | — |
| Glycerol monooleate (HLB = 2.5) | — | — | — | 1 | 0.05 |
| Sorbitan monostearate (HLB = 4.9) | — | — | 3 | — | — |
| Component (c) | | | | | |
| Polyoxyethylene (p̄ = 15) lauryl ether (HLB = 6.8) | — | — | — | — | — |
| Polyethylene glycol (MW = 3000) monostearate (HLB = 23.7) | — | 5 | — | — | 0.05 |
| Polyoxyethylene (p̄ = 20) polyoxypropylene (p̄ = 5) myristyl ether (HLB = 8.2) | — | — | — | 12 | — |
| Polyoxyethylene (p̄ = 20) sorbitan monolaurate (HLB = 14.3) | — | — | 5 | — | — |
| Component (d) | | | | | |
| NaCl | 0.5 | — | — | — | — |
| $K_2SO_4$ | — | — | — | — | 0.5 |
| Sodium citrate | — | 0.5 | — | — | — |
| Sodium p-toluenesulfonate | — | — | — | — | — |
| Disodium edate | — | — | — | 0.5 | — |
| Water | Balance | Balance | Balance | Balance | Balance |
| pH 1) (neat liquid) | 6.9 | 7.2 | 7.5 | 7.0 | 6.7 |
| Evaluation | | | | | |
| Foaming ability (mm) | 80 | 82 | 87 | 75 | 79 |
| Rinsability (times) | 7 | 7 | 7 | 8 | 7 |
| Felling to the hands | | | | | |
| During use | +2.0 | +1.6 | +3.5 | +1.5 | +0 |
| After use | +2.3 | +1.5 | +3.5 | +1.5 | +0 |
| Drainability | C | C | C | C | C |

1) pH was appropriately adjusted with $H_2SO_4$ or NaOH.
2) p indicates the average moles of addition.

Example 2

Light duty liquid detergent composition for laundry

| | % by weight |
|---|---|
| Alkyl glycoside 1) | 20 |
| Sodium polyoxyethylene (p = 2)-alkyl($C_{12-13}$)ether sulfate | 10 |
| Softhanol 33 2) | 2 |
| Polyoxyethylene (p = 30)-lauryl ether (HLB = 11.7) | 3 |
| Sodium malate | 3 |
| Ethanol | 4 |
| Perfume, enzyme | Small amount |
| Water | Balance |
| | 100 |

(The above mixture was adjusted to pH 8.0)
1) In formula (I), $x = 1$, $y = 1.30$, $R_1 = C_{10-12}$ alkyl, $R_2 = C_2$ alkylene, G = glucose residue
2) Trademark, a nonionic surfactant produced by Nippon Shokubai Kagaku Kogyo Co., Ltd. (HLB: about 2.4)

Example 3

Dishwasing detergent composition

| | % by weight |
|---|---|
| Alkyl glycoside 1) | 20 |
| Sodium polyoxyethylene (p = 5)-laurylether sulfate | 5 |
| Glycerol monomyristate (HLB = 4.4) | 2 |
| Polyoxyethylene (p = 60) hydrogenated castor oil | 5 |
| Lauryldimethylamine oxide | 2 |
| Sodium sulfate | 1 |
| Ethanol | 3 |
| Perfume, enzyme | Small amount |
| Water | Balance |
| | 100 |

(The above mixture was adjusted to pH 7.0)
1) In formula (I), $x = 0$, $y = 1.4$, $R_1 = C_{9-11}$ alkyl, G = glucose residue Obviously, numerous modifications and variations of the present invention are possible in light of the above teachings. It is therefore to be understood that within the scope of the appended claims, the invention may be practiced otherwise than as specifically described herein.

What is claimed is:

1. A neutral liquid detergent composition comprising:
   (a) 2-60% by weight of an alkyl glycoside represented by the following formula (I):

$$R_1(OR_2)_xG_y \quad (I)$$

wherein $R_1$ is a linear or branched alkyl, alkenyl, or alkylphenyl group having 8-18 carbon atoms, $R_2$ is an alkylene group having 2-4 carbon atoms, G is a reducing saccharide residue having 5-6 carbon atoms, x is a number of which the mean value is 0-5, and y is a number of which the mean value is 1.0-1.42;

(b) 0.1-10% by weight of a nonionic surfactant having an HLB of less than 5 selected from the group consisting of polyoxyethylene alkyl ether, polyoxyethylene alkylphenyl ether, polyoxyethylene sorbitan fatty acid ester, polyoxyethylene sorbit fatty acid ester, polyoxyethylene glycol fatty acid ester, polyoxyethylene polyoxypropylene alkyl ether, polyoxyethylene castor oil, polyoxyethylene hydrogenated castor oil, polyoxyethylene alkylamine and glycerol fatty acid ester;

(c) 0.1 to 10% by weight of a nonionic surfactant having an HLB of not less than 5 selected from the group consisting of polyoxyethylene alkyl ether, polyoxyethylene alkylphenyl ether, polyoxyethylene sorbitan fatty acid ester, polyoxyethylene sorbit fatty acid ester, polyethylene glycol fatty acid ester, polyoxyethylene polyoxypropylene alkyl ether, polyoxyethylene castor oil, polyoxyethylene hydrogenated castor oil, polyoxyethylene alkylamine and polyoxyethylene fatty acid amide having total adduct mols of ethylene oxide of not less than 10, with the proviso that the difference in HLB between component (b) and component (c) is greater than 3; and (d) 0.001-8% by weight of one or more water-soluble organic or inorganic salts selected from the group consisting of sulfates, chlorides, borates, phosphates, P-toluensulfonates, m-xylenesulfonates, benzoates, malates, succinates, tartarates, citrates, lactates, and edates of sodium and potassium and mixtures thereof; the ratio by weight of component /(a) being in a range of 1/10-1/1 and the ratio by weight of component (b)/(c) being in a range of 1/10-1/1.

2. A neutral liquid detergent composition according to claim 1, further comprising one or more surfactants selected from 1-20% by weight of anionic surfactants, 1-20% by weight of amphoteric surfactants, and 1-10% by weight of nonionic surfactants other than components (a)-(c).

* * * * *

UNITED STATES PATENT AND TRADEMARK OFFICE
CERTIFICATE OF CORRECTION

PATENT NO. : 5,154,850
DATED : October 13, 1992
INVENTOR(S) : Katsuhiko DEGUCHI, et al.

It is certified that error appears in the above-identified patent and that said Letters Patent is hereby corrected as shown below:

Column 10, line 41, "/(a)"; should read, --[(b) + (c)]/(a)--.

Signed and Sealed this

Ninth Day of November, 1993

*Attest:*

BRUCE LEHMAN

*Attesting Officer*   *Commissioner of Patents and Trademarks*